US010210736B2

(12) United States Patent
Qin et al.

(10) Patent No.: US 10,210,736 B2
(45) Date of Patent: Feb. 19, 2019

(54) MONITORING METHOD AND RELATED DEVICE FOR INTELLIGENT MONITORING SYSTEM

(71) Applicant: Huawei Technologies Co., Ltd., Shenzhen (CN)

(72) Inventors: Muyun Qin, Shenzhen (CN); Rongan Peng, Shenzhen (CN); Ruimin Wang, Shenzhen (CN); Jianhui Jiang, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 0 days.

(21) Appl. No.: 15/564,289

(22) PCT Filed: Apr. 8, 2015

(86) PCT No.: PCT/CN2015/076026
§ 371 (c)(1),
(2) Date: Oct. 4, 2017

(87) PCT Pub. No.: WO2016/161568
PCT Pub. Date: Oct. 13, 2016

(65) Prior Publication Data
US 2018/0137731 A1    May 17, 2018

(51) Int. Cl.
| G08B 21/02 | (2006.01) |
| A61B 5/00 | (2006.01) |
| A61B 5/01 | (2006.01) |
| G08B 21/04 | (2006.01) |
| A61B 5/11 | (2006.01) |

(52) U.S. Cl.
CPC ........ *G08B 21/0205* (2013.01); *A61B 5/0022* (2013.01); *A61B 5/01* (2013.01);
(Continued)

(58) Field of Classification Search
CPC ............ G08B 21/0205; G08B 21/0219; A61B 5/0015; A61B 5/01; A61B 2503/04
(Continued)

(56) References Cited

U.S. PATENT DOCUMENTS

| 2011/0015467 A1 | 1/2011 | Dothie et al. | |
| 2014/0121473 A1* | 5/2014 | Banet | A61B 5/0015 600/301 |
| 2016/0364617 A1* | 12/2016 | Silberschatz | A61B 5/0205 |

FOREIGN PATENT DOCUMENTS

| CN | 2758881 Y | 2/2006 |
| CN | 201576343 U | 9/2010 |

(Continued)

OTHER PUBLICATIONS

Machine Translation and Abstract of Chinese Publication No. CN103824417, May 28, 2014, 6 pages.
(Continued)

*Primary Examiner* — John A Tweel, Jr.
(74) *Attorney, Agent, or Firm* — Conley Rose, P.C.

(57) ABSTRACT

A monitoring method and a device for an intelligent monitoring system includes establishing a Bluetooth low energy (BLE) link between a front-end monitoring device and a back-end monitoring device; receiving, by the front-end monitoring device by using the BLE link, a first body temperature value sent by the back-end monitoring device; measuring, by the front-end monitoring device, body temperature of a monitoring person to obtain a second body temperature value; and determining, by the front-end monitoring device according to a variation of the first body temperature value relative to the second body temperature value, whether first prompt information needs to be generated.

15 Claims, 5 Drawing Sheets

(52) U.S. Cl.
CPC .......... *A61B 5/681* (2013.01); *G08B 21/0211* (2013.01); *G08B 21/0219* (2013.01); *G08B 21/0453* (2013.01); *A61B 5/0002* (2013.01); *A61B 5/0015* (2013.01); *A61B 5/11* (2013.01); *A61B 5/4815* (2013.01); *A61B 5/6823* (2013.01); *A61B 5/6828* (2013.01); *A61B 2503/04* (2013.01); *A61B 2503/06* (2013.01); *A61B 2562/0219* (2013.01)

(58) Field of Classification Search
USPC ..................................................... 340/573.1
See application file for complete search history.

(56) References Cited

FOREIGN PATENT DOCUMENTS

| | | |
|---|---|---|
| CN | 202843588 U | 4/2013 |
| CN | 103646494 A | 3/2014 |
| CN | 103824417 A | 5/2014 |
| CN | 103903402 A | 7/2014 |
| CN | 103914946 A | 7/2014 |
| CN | 104217529 A | 12/2014 |
| CN | 204091952 U | 1/2015 |
| JP | 2008048819 A | 3/2008 |
| WO | 2014151925 A1 | 9/2014 |

OTHER PUBLICATIONS

Machine Translation and Abstract of Chinese Publication No. CN104217529, Dec. 17, 2014, 17 pages.
Machine Translation and Abstract of Chinese Publication No. CN202843588, Apr. 3, 2013, 8 pages.
Foreign Communication From a Counterpart Application, PCT Application No. PCT/CN2015/076026, English Translation of International Search Report dated Jan. 13, 2016, 2 pages.
Foreign Communication From a Counterpart Application, PCT Application No. PCT/CN2015/076026, English Translation of Written Opinion dated Jan. 13, 2016, 5 pages.
Foreign Communication From a Counterpart Application, Eurpean Application No. 15888125.0, Extended European Search Report dated May 2, 2018, 13 pages.
Machine Translation and Abstract of Chinese Publication No. CN2758881, Feb. 15, 2006, 22 pages.
Machine Translation and Abstract of Chinese Publication No. CN103646494, Mar. 19, 2014, 8 pages.
Machine Translation and Abstract of Chinese Publication No. CN103903402, Jul. 2, 2014, 7 pages.
Machine Translation and Abstract of Chinese Publication No. CN103914946, Jul. 9, 2014, 15 pages.
Machine Translation and Abstract of Chinese Publication No. CN201576343, Sep. 8, 2010, 11 pages.
Machine Translation and Abstract of Chinese Publication No. CN204091952, Jan. 14, 2015, 10 pages.
Machine Translation and Abstract of Japanese Publication No. JP2008048819, Mar. 6, 2008, 14 pages.
Foreign Communication From a Counterpart Application, Chinese Application No. 201580004147.0, Chinese Office Action dated Mar. 19, 2018, 8 pages.

\* cited by examiner

MONITORING METHOD AND RELATED DEVICE FOR INTELLIGENT MONITORING SYSTEM

CROSS-REFERENCE TO RELATED APPLICATIONS

This application is a national stage application of International Patent Application No. PCT/CN2015/076026, filed on Apr. 8, 2015, which is herein incorporated by reference in its entirety.

TECHNICAL FIELD

The present disclosure relates to the field of communications technologies, and in particular, to a monitoring method and a related device for an intelligent monitoring system.

BACKGROUND

Under normal physiological conditions, during sleep, body temperature drops and resistance to bacteria and viruses also drops because metabolism of a human body slows down. If a person is not well tucked up during sleep, the person is extremely likely to catch a disease such as cold. Resistance of a child is poorer than resistance of an adult. Therefore, if a child kicks off a quilt during sleep and a parent does not tuck up the child well in time, the child is more likely to catch a cold.

An implementation process of an existing quilt-kicking prevention system is, before sleeping, a child wears a device on which a light sensor is installed; when a quilt is kicked off, intensity of light received by the light sensor becomes greater, and in this case, the quilt-kicking prevention system gives a sound alarm to remind a parent to tuck the child up.

An implementation process of another existing quilt-kicking prevention system is, before sleeping, a child wears a device on which a thermistor sensor, a differential amplifier, and a dedicated frequency modulation (FM) transceiver circuit are installed; when a quilt is kicked off, a resistance value of the thermistor sensor changes; the differential amplifier is used to start an encoder and drive a dedicated FM transmitter; the FM transmitter transmits a signal to an FM receiver at a parent end; and a device at the parent end starts a decoder, and makes a prompt sound to remind the parent to tuck the child up.

However, in the foregoing system in which the light sensor is used, the light sensor cannot normally alarm in extremely strong light (in daytime in which luminance is greater than 10000 luxes) or extremely weak light (at night without illumination in which luminance is less than 20 luxes). Consequently, the system is limited. If a reminding sound of the device is extremely low, the parent cannot be reminded. If a reminding sound is extremely loud, the child in sleep is likely to be awoken and sleep of the child is affected. In the foregoing system in which the thermistor sensor, the differential amplifier, and the dedicated FM transceiver circuit are used, the thermistor sensor that uses the differential amplifier varies within a large range. Consequently, a variation of an absolute temperature value cannot be precisely measured, a false alarm is prone to be caused, and use of the dedicated FM transceiver device leads to poor convenience, high costs, and large power consumption.

SUMMARY

Embodiments of the present disclosure provide a monitoring method and a related device for an intelligent monitoring system. The monitoring method and the related device are used by a monitoring device to analyze a temperature variation of a monitoring person and a temperature variation of a monitored person, so that the monitoring person receives prompt information of a state variation of the monitored person in time, and determining accuracy and precision of the intelligent monitoring system are improved.

In view of this, a first aspect of the present disclosure provides a front-end monitoring device, including a Bluetooth low energy (BLE) module configured to establish a BLE link between the front-end monitoring device and a back-end monitoring device; a universal asynchronous receiver/transmitter (UART) configured to receive, by using the BLE link, a first body temperature value sent by the back-end monitoring device, where the first body temperature value is obtained by the back-end monitoring device by measuring body temperature of a monitored person; a thermistor sensor configured to measure body temperature of a monitoring person to obtain a second body temperature value; and a processing module configured to determine, according to a variation of the first body temperature value relative to the second body temperature value, whether first prompt information needs to be generated.

With reference to the first aspect of the present disclosure, in a first implementation manner of the first aspect of the present disclosure, the processing module includes a digital calculator, a determiner, and a signal generator; the digital calculator is configured to calculate a temperature difference between the first body temperature value and the second body temperature value, and generate a temperature difference sequence according to multiple calculated temperature differences; the determiner is configured to determine whether M consecutive temperature differences in the temperature difference sequence progressively increase, where M is a positive integer greater than or equal to 2; and the signal generator is configured to generate the first prompt information when the M consecutive temperature differences in the temperature difference sequence progressively increase.

With reference to the first implementation manner of the first aspect of the present disclosure, in a second implementation manner of the first aspect of the present disclosure, the determiner is further configured to determine whether the second body temperature value is in a normal body temperature value range; and the signal generator is further configured to generate second prompt information when the second body temperature value is outside the normal body temperature value range.

With reference to the first implementation manner of the first aspect of the present disclosure, in a third implementation manner of the first aspect of the present disclosure, the digital calculator is further configured to generate a body temperature sequence according to multiple consecutively received first body temperature values; and the determiner is further configured to determine whether N consecutive first body temperature values in the body temperature sequence progressively decrease, where N is a positive integer greater than or equal to 2.

With reference to the first implementation manner of the first aspect of the present disclosure, the second implementation manner of the first aspect, or the third implementation manner of the first aspect, in a fourth implementation manner of the first aspect of the present disclosure, the UART is further configured to receive, by using the BLE link, action information sent by the back-end monitoring device, and the action information is obtained by the back-end monitoring device by measuring the monitored person by using an acceleration sensor.

With reference to the fourth implementation manner of the first aspect of the present disclosure, in a fifth implementation manner of the first aspect of the present disclosure, the determiner is further configured to determine whether the action information meets a preset condition; and the signal generator is further configured to generate third prompt information when the M consecutive temperature differences in the temperature difference sequence progressively increase and the action information meets the preset condition.

A second aspect of the present disclosure provides a back-end monitoring device, including a BLE module configured to establish a BLE link between the back-end monitoring device and a front-end monitoring device; a thermistor sensor configured to measure body temperature of a monitored person to obtain a first body temperature value; and a UART configured to send the first body temperature value to the front-end monitoring device by using the BLE link.

With reference to the second aspect of the present disclosure, in a first implementation manner of the second aspect of the present disclosure, the back-end monitoring device further includes an acceleration sensor; the acceleration sensor is configured to measure an action of the monitored person to obtain action information; and the UART is further configured to send the action information to the front-end monitoring device by using the BLE link.

A third aspect of the present disclosure provides an intelligent monitoring system, including the front-end monitoring device according to any one of the first aspect of the present disclosure to the fifth implementation manner of the first aspect of the present disclosure and the back-end monitoring device according to either of the second aspect of the present disclosure and the first implementation manner of the second aspect of the present disclosure.

A fourth aspect of the present disclosure provides a monitoring method for an intelligent monitoring system, including establishing a BLE link between a front-end monitoring device and a back-end monitoring device; receiving, by the front-end monitoring device by using the BLE link, a first body temperature value sent by the back-end monitoring device, where the first body temperature value is obtained by the back-end monitoring device by measuring body temperature of a monitored person; measuring, by the front-end monitoring device, body temperature of a monitoring person to obtain a second body temperature value; and determining, by the front-end monitoring device according to a variation of the first body temperature value relative to the second body temperature value, whether first prompt information needs to be generated.

With reference to the fourth aspect of the present disclosure, in a first implementation manner of the fourth aspect of the present disclosure, the determining, by the front-end monitoring device according to a variation of the first body temperature value relative to the second body temperature value, whether first prompt information needs to be generated includes calculating, by the front-end monitoring device, a temperature difference between the first body temperature value and the second body temperature value, and generating a temperature difference sequence according to multiple calculated temperature differences; determining, by the front-end monitoring device, whether M consecutive temperature differences in the temperature difference sequence progressively increase, where M is a positive integer greater than or equal to 2; and if yes, generating, by the front-end monitoring device, the first prompt information.

With reference to the first implementation manner of the fourth aspect of the present disclosure, in a second implementation manner of the fourth aspect of the present disclosure, before the calculating, by the front-end monitoring device, a temperature difference between the first body temperature value and the second body temperature value, and generating a temperature difference sequence according to multiple calculated temperature differences, the method includes determining, by the front-end monitoring device, whether the second body temperature value is in a normal body temperature value range; and generating, by the front-end monitoring device, second prompt information if the second body temperature value is outside the normal body temperature value range.

With reference to the first implementation manner of the fourth aspect of the present disclosure, in a third implementation manner of the fourth aspect of the present disclosure, before the determining, by the front-end monitoring device, whether M consecutive temperature differences in the temperature difference sequence progressively increase, the method further includes generating, by the front-end monitoring device, a body temperature sequence according to multiple consecutively received first body temperature values; determining, by the front-end monitoring device, whether N consecutive first body temperature values in the body temperature sequence progressively decrease, where N is a positive integer greater than or equal to 2; and if the N consecutive first body temperature values in the body temperature sequence progressively decrease, performing the step of determining, by the front-end monitoring device, whether M consecutive temperature differences in the temperature difference sequence progressively increase.

With reference to the first implementation manner of the fourth aspect of the present disclosure, the second implementation manner of the fourth aspect, or the third implementation manner of the fourth aspect, in a fourth implementation manner of the fourth aspect of the present disclosure, the method further includes receiving, by the front-end monitoring device by using the BLE link, action information sent by the back-end monitoring device, where the action information is obtained by the back-end monitoring device by measuring the monitored person by using an acceleration sensor.

With reference to the fourth implementation manner of the fourth aspect of the present disclosure, in a fifth implementation manner of the fourth aspect of the present disclosure, before the generating, by the front-end monitoring device, the first prompt information, the method further includes determining, by the front-end monitoring device, whether the action information meets a preset condition; and generating, by the front-end monitoring device, third prompt information when the M consecutive temperature differences in the temperature difference sequence progressively increase and if the action information meets the preset condition.

A fifth aspect of the present disclosure provides a monitoring method for an intelligent monitoring system, including establishing a BLE link between a back-end monitoring device and a front-end monitoring device; obtaining, by the back-end monitoring device, a first body temperature value, where the first body temperature value is obtained by the back-end monitoring device by measuring body temperature of a monitored person; and sending, by the back-end monitoring device, the first body temperature value to the front-end monitoring device by using the BLE link.

With reference to the fifth aspect of the present disclosure, in a first implementation manner of the fifth aspect of the present disclosure, the method further includes obtaining, by the back-end monitoring device, action information, where the action information is obtained by the back-end monitoring device by measuring the monitored person by using an acceleration sensor; and sending, by the back-end monitoring device, the action information to the front-end monitoring device by using the BLE link.

It can be learned from the foregoing technical solutions that the embodiments of the present disclosure have the following advantages.

In the embodiments of the present disclosure, a BLE link is established between a front-end monitoring device and a back-end monitoring device. The front-end monitoring device receives, by using the BLE link, a first body temperature value sent by the back-end monitoring device, and the first body temperature value is obtained by the back-end monitoring device by measuring body temperature of a monitored person. The front-end monitoring device measures body temperature of a monitoring person to obtain a second body temperature value. The front-end monitoring device determines, according to a variation of the first body temperature value relative to the second body temperature value, whether first prompt information needs to be generated. The first body temperature value obtained by the back-end monitoring device by measuring the body temperature of the monitored person and the second body temperature value obtained by the front-end monitoring device by measuring the body temperature of the monitoring person are analyzed, and whether to generate the first prompt information is determined according to variations, obtained by means of analysis, of the first body temperature value and the second body temperature value. Both the measured first body temperature value and the measured second body temperature value are put into calculation in a determining step. Therefore, accuracy and precision of a monitoring result are improved.

BRIEF DESCRIPTION OF DRAWINGS

To describe the technical solutions in the embodiments of the present disclosure more clearly, the following briefly describes the accompanying drawings required for describing the embodiments and the prior art. The accompanying drawings in the following description show merely some embodiments of the present disclosure, and persons of ordinary skill in the art may still derive other drawings from these accompanying drawings without creative efforts.

DESCRIPTION OF EMBODIMENTS

Embodiments of the present disclosure provide a monitoring method and a related device for an intelligent monitoring system. The monitoring method and the related device are used by a monitoring device to analyze a temperature variation of a monitoring person and a temperature variation of a monitored person, so that the monitoring person receives prompt information of a state variation of the monitored person in time, and accuracy and precision of the intelligent monitoring system are improved.

In the embodiments of the present disclosure, the monitoring person wears a front-end monitoring device, and the monitored person wears a back-end monitoring device. A thermistor sensor in the front-end monitoring device needs to be in contact with skin of the monitoring person and a thermistor sensor in the back-end monitoring device needs to be in contact with skin of the monitored person, so that the devices can measure body temperature of the monitoring person and body temperature of the monitored person.

Figure 1:
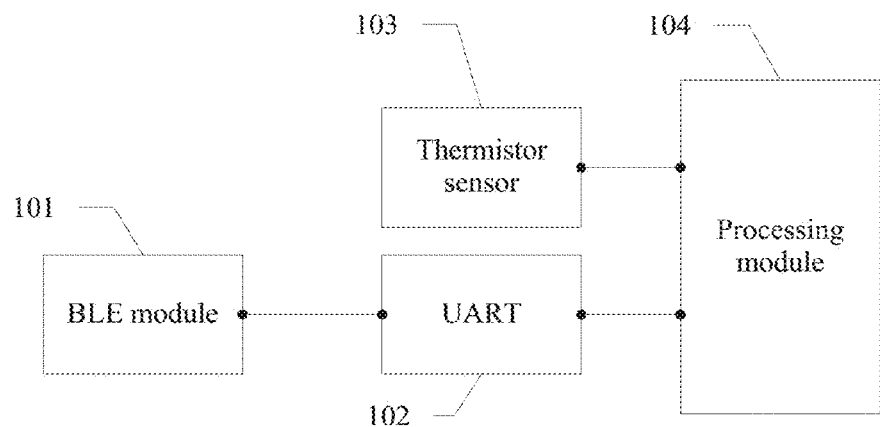
FIG. 1 is a schematic structural diagram of a front-end monitoring device according to an embodiment of the present disclosure.
Figure 2:
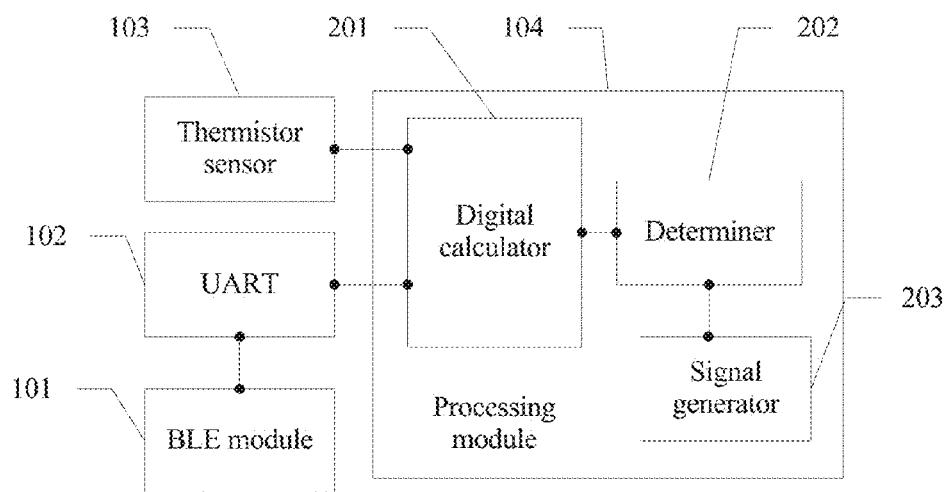
FIG. 2 is a schematic structural diagram of a front-end monitoring device according to another embodiment of the present disclosure.

Referring to FIG. 1, an embodiment of a front-end monitoring device in an embodiment of the present disclosure includes a BLE module 101 configured to establish a BLE link between the front-end monitoring device and a back-end monitoring device; a UART 102 configured to receive, by using the BLE link, a first body temperature value sent by the back-end monitoring device, where the first body temperature value is obtained by the back-end monitoring device by measuring body temperature of a monitored person; a thermistor sensor 103 configured to measure body temperature of a monitoring person to obtain a second body temperature value; and a processing module 104 configured to determine, according to a variation of the first body temperature value relative to the second body temperature value, whether first prompt information needs to be generated.

In this embodiment of the present disclosure, a first body temperature value obtained by a back-end monitoring device by measuring body temperature of a monitored person and a second body temperature value obtained by a front-end monitoring device by measuring body temperature of a monitoring person are analyzed. Whether to generate first prompt information is determined according to variations, obtained by means of analysis, of the first body temperature value and the second body temperature value. Both the measured first body temperature value and the measured second body temperature value are put into calculation in a determining step. Therefore, accuracy and precision of a monitoring result are improved.

Optionally, the foregoing processing module 104 includes a digital calculator 201, a determiner 202, and a signal generator 203.

The digital calculator 201 is configured to calculate a temperature difference between the first body temperature value and the second body temperature value, and generate a temperature difference sequence according to multiple calculated temperature differences.

The determiner 202 is configured to determine whether M temperature differences in the temperature difference sequence progressively increase. M is a positive integer greater than or equal to 2, and M may be a positive integer greater than or equal to 3.

The signal generator 203 is configured to generate the first prompt information when the M consecutive temperature differences in the temperature difference sequence progressively increase.

In this embodiment of the present disclosure, the processing module 104 is subdivided into the digital calculator 201, the determiner 202, and the signal generator 203, so that this solution is more specific.

Optionally, the determiner 202 is further configured to determine whether the second body temperature value is in a normal body temperature value range.

The signal generator 203 is further configured to generate second prompt information when the second body temperature value is outside the normal body temperature value range.

In this embodiment of the present disclosure, the determiner 202 performs determining on the second body temperature value, so that this solution is improved.

Optionally, the digital calculator 201 is further configured to generate a body temperature sequence according to multiple consecutively received first body temperature values.

The determiner 202 is further configured to determine whether N consecutive first body temperature values in the body temperature sequence progressively decrease. N is a positive integer greater than or equal to 2, and preferably, M may be a positive integer greater than or equal to 3.

In this embodiment of the present disclosure, the determiner 202 performs determining on the body temperature sequence of the first body temperature values that is obtained by the digital calculator 201, so that this solution is more detailed.

Optionally, the UART 102 is further configured to receive, by using the BLE link, action information sent by the back-end monitoring device, and the action information is obtained by the back-end monitoring device by measuring the monitored person by using an acceleration sensor.

Optionally, the determiner 202 is further configured to determine whether the action information meets a preset condition.

The signal generator 203 is further configured to send third prompt information when the M consecutive temperature differences in the temperature difference sequence progressively increase and the action information meets the preset condition.

In this embodiment of the present disclosure, the determining on the action information of the monitored person further improves accuracy of this solution.

Figure 3:
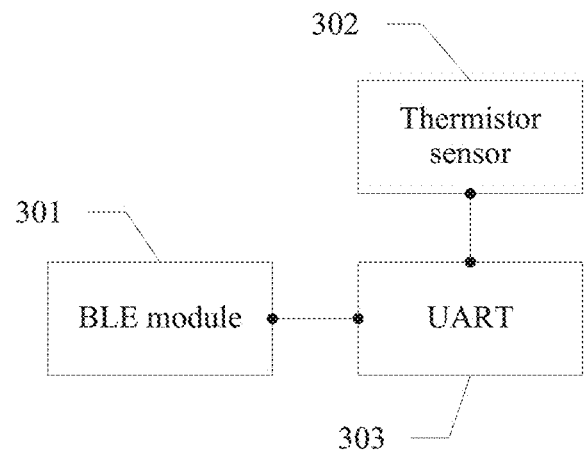
FIG. 3 is a schematic structural diagram of a back-end monitoring device according to an embodiment of the present disclosure.

Referring to FIG. 3, an embodiment of a back-end monitoring device in an embodiment of the present disclosure includes a BLE module 301 configured to establish a BLE link between the back-end monitoring device and a front-end monitoring device; a thermistor sensor 302 configured to measure body temperature of a monitored person to obtain a first body temperature value; and a UART 303 configured to send the first body temperature value obtained by the thermistor sensor 302 to the front-end monitoring device by using the BLE link.

In this embodiment of the present disclosure, the back-end monitoring device sends the obtained first body temperature value to the front-end monitoring device by using the BLE link established by the BLE module 301, so that the front-end monitoring device performs processing. Energy consumption of the devices is reduced in a BLE communication manner.

Figure 4:
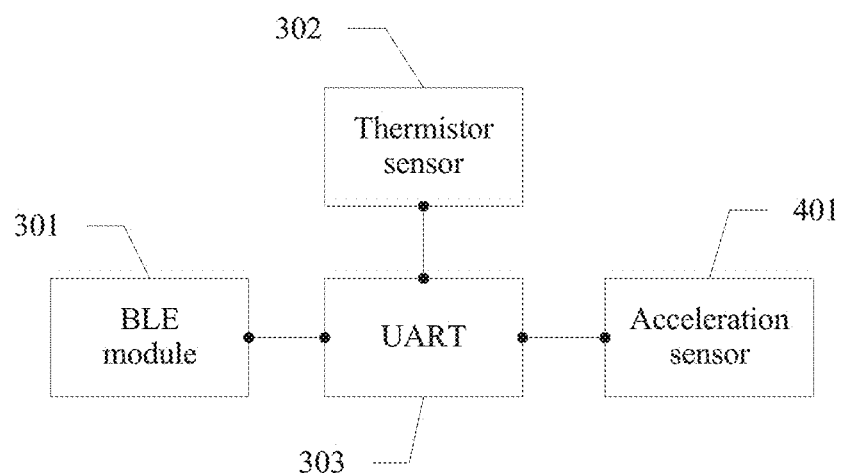
FIG. 4 is a schematic structural diagram of a back-end monitoring device according to another embodiment of the present disclosure.

Optionally, as shown in FIG. 4, the back-end monitoring device further includes an acceleration sensor 401.

The acceleration sensor 401 is configured to measure an action of the monitored person to obtain action information.

The UART 303 is further configured to send the action information to the front-end monitoring device by using the BLE link.

In this embodiment of the present disclosure, the acceleration sensor 401 monitors the action of the monitored person and obtains the action information, so that this solution is more specific.

The following describes a process of interaction between modules of intelligent monitoring devices according to the embodiments of the present disclosure in a specific implementation manner.

Figure 6:
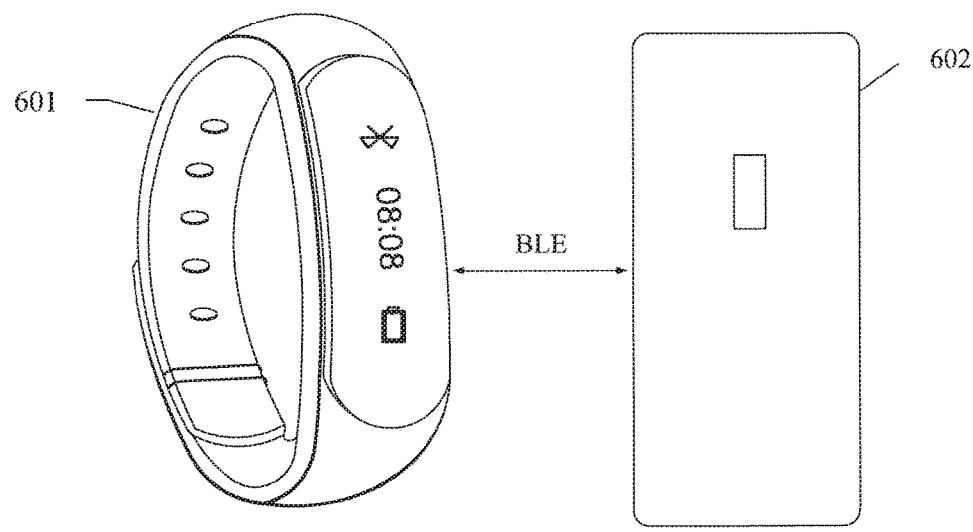
FIG. 6 is a schematic object diagram of a front-end monitoring device and a back-end monitoring device.

For ease of description, this embodiment is described by using child quilt-kicking monitoring as an example. As shown in FIG. 6, a front-end monitoring device 601, that is, a device at a parent end, is a generally universal smart band. A flat thin heat (FTH) thermistor is installed on an inner side that is of the smart band and that is in contact with skin. A back-end monitoring device 602, that is, a device at a child end, is a shell temperature detector that can be put in an elastic wristband. As shown in FIG. 4, an FTH thermistor, that is, a thermistor sensor 302, and a built-in acceleration sensor 401 are installed on an inner side that is of the shell temperature detector and that is in contact with skin. The front-end monitoring device 601 and the back-end monitoring device 602 are connected by using a BLE link.

Figure 5:
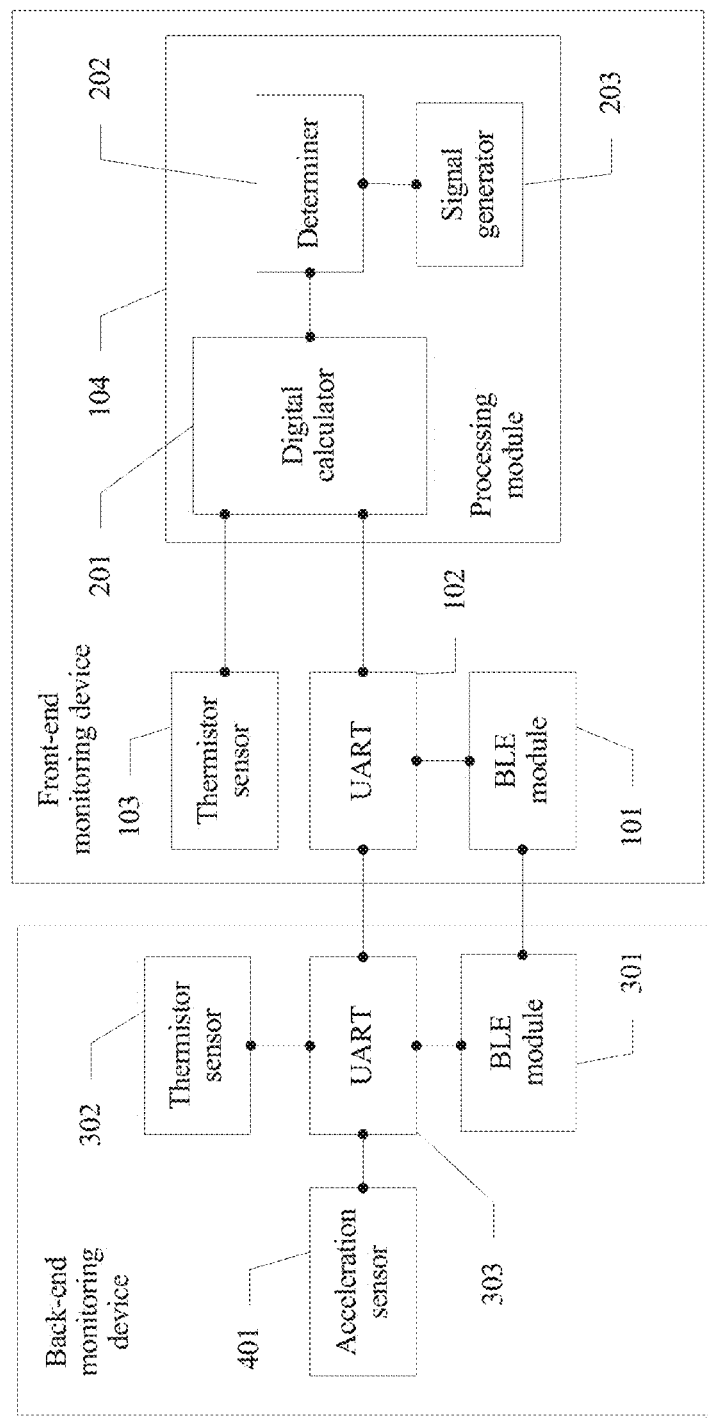
FIG. 5 is a schematic diagram of interaction between a module of a front-end monitoring device and a module of a back-end monitoring device according to an embodiment of the present disclosure.

Before a child goes to sleep, the back-end monitoring device 602 is fastened on a body or a leg of the child, and the front-end monitoring device 601 is worn on a wrist of a parent. In this case, in FIG. 5, a BLE link is established between a BLE module 301 of the back-end monitoring device and a BLE module 101 of the front-end monitoring device.

Generally, normal body temperature of a child is approximately 36.5 degrees Celsius and normal body temperature of a wrist of an adult is approximately 36 degrees Celsius. After the child kicks off a quilt, shell temperature of the child measured by the thermistor sensor 302 of the back-end monitoring device drops rapidly.

The thermistor sensor 302 and a thermistor sensor 103 are set for collecting obtained body temperature once a second, to obtain a 1st body temperature value and a second body temperature value. For example, in the first second, a body temperature value A1 of the child obtained by the thermistor sensor 302 is 36.0, a UART 303 sends A1 to a UART 102 by using the BLE link, and the UART 102 sends the obtained A1 to a digital calculator 201 in a processing module 104. In the first second, a body temperature value B1 of the parent obtained by the thermistor sensor 103 is 36.1, and the digital calculator 201 obtains B1. The digital calculator 201 learns, by means of calculation, that a temperature difference C1 between A1 and B1 is 0.1.

When the child kicks off the quilt in the 2nd second, a body temperature value A2 of the child obtained by the thermistor sensor 302 is 35.9, the UART 303 sends A2 to the UART 102 by using the BLE link, and the UART 102 sends the obtained A2 to the digital calculator 201. In the 2nd second, a body temperature value B2 of the parent obtained by the thermistor sensor 103 is 36.1, and the digital calculator 201 obtains B2. The digital calculator 201 learns, by means of calculation, that a temperature difference C2 between A2 and B2 is 0.2.

In the third second, a body temperature value A3 of the child obtained by the thermistor sensor 302 is 35.7, the UART 303 sends A3 to the UART 102 by using the BLE link, and the UART 102 sends the obtained A3 to the digital calculator 201. In the third second, a body temperature value B3 of the parent obtained by the thermistor sensor 103 is 36.2, and the digital calculator 201 obtains B3. The digital calculator 201 learns, by means of calculation, that a temperature difference C3 between A3 and B3 is 0.5.

In the fourth second, a body temperature value A4 of the child obtained by the thermistor sensor 302 is 35.4, the UART 303 sends A4 to the UART 102 by using the BLE link, and the UART 102 sends the obtained A4 to the digital calculator 201. In the fourth second, a body temperature value B4 of the parent obtained by the thermistor sensor 103 is 36.1, and the digital calculator 201 obtains B4. The digital calculator 201 learns, by means of calculation, that a temperature difference C4 between A4 and B4 is 0.7.

In the fifth second, a body temperature value A5 of the child obtained by the thermistor sensor 302 is 35.1, the UART 303 sends A5 to the UART 102 by using the BLE link, and the UART 102 sends the obtained A5 to the digital calculator 201. In the fifth second, a body temperature value B5 of the parent obtained by the thermistor sensor 103 is 36.0, and the digital calculator 201 obtains B5. The digital calculator 201 learns, by means of calculation, that a temperature difference C5 between A5 and B5 is 0.9.

The determiner 202 determines whether a body temperature value in B1, B2, B3, and B5 is beyond a normal body temperature value range, and the normal body temperature value range is set to "35.0 to 37.5". If B2 is 38.0, it indicates that the parent has a fever, and the body temperature value of the parent cannot be used for calculation. The signal generator 203 generates second prompt information. In this example, the second prompt information is a buzzing sound that is made once every two seconds, so as to remind the parent that a body temperature value at the parent end is abnormal. In this embodiment, B1, B2, B3, B4, and B5 are all in the normal body temperature value range. The digital calculator 201 generates a temperature difference sequence by using C1, C2, C3, C4, and C5, and generates a body temperature sequence by using A1, A2, A3, A4, and A5. The determiner 202 determines whether consecutive four first body temperature values in the body temperature sequence progressively decrease. A2 to A5 progressively decrease. Therefore, the determiner 202 continues to determine whether consecutive three temperature differences in the temperature difference sequence progressively increase. Any consecutive three temperature differences from C1 to C5 progressively increase. Therefore, the signal generator 203 generates first prompt information. In this example, the first prompt information is a buzzing sound that is made once every 0.5 second, so as to remind the parent of a drop in the body temperature of the child.

The acceleration sensor 401 in the back-end monitoring device records action information when the child performs an action. The UART 303 in the back-end monitoring device sends the action information to the UART 102 in the front-end monitoring device by using the BLE link. The determiner 202 determines whether the action information received by the UART 102 meets a preset condition for a preset turn-over action. When the consecutive three temperature differences in the temperature difference sequence progressively increase, and if the action information meets the preset condition, the signal generator 203 generates third prompt information. It is assumed that the third prompt information is vibration. Because the consecutive three temperature differences in the temperature difference sequence progressively increase, the signal generator 203 generates the first prompt information. In this case, the first prompt information and the third prompt information may be sent together. The signal generator 203 generates a buzzing sound and vibration once every 0.5 second, so as to remind the parent that the child kicks off the quilt. When the consecutive three temperature differences in the temperature difference sequence progressively increase, and if the action information does not reach the preset condition, the signal generator 203 generates the first prompt information, that is, the buzzing sound that is made once every 0.5 second.

The foregoing intelligent monitoring system is used for child quilt-kicking monitoring, and may be further used for child fever temperature variation monitoring. For example, when a child has a fever, a determiner 202 in a front-end monitoring device may be set for monitoring a first body temperature value and the determiner 202 sets a first body temperature value range to "35.0 to 38.0". When the child has a low fever or a high fever, a thermistor sensor 302 sends a measured first body temperature value to a digital calculator 201. When the determiner 202 determines that the first body temperature value is not in the specified first body temperature value range, a signal generator 203 generates prompt information to remind the parent.

A microprocessor in the back-end monitoring device is correspondingly programmed, so that the back-end monitoring device may further have functions such as child fever temperature variation monitoring, child step counting, and child sleep quality monitoring. Details are not described herein.

A monitoring method in an embodiment of the present disclosure is based on an intelligent monitoring system that is established by a front-end monitoring device and a back-end monitoring device by using a BLE link.

Figure 7:
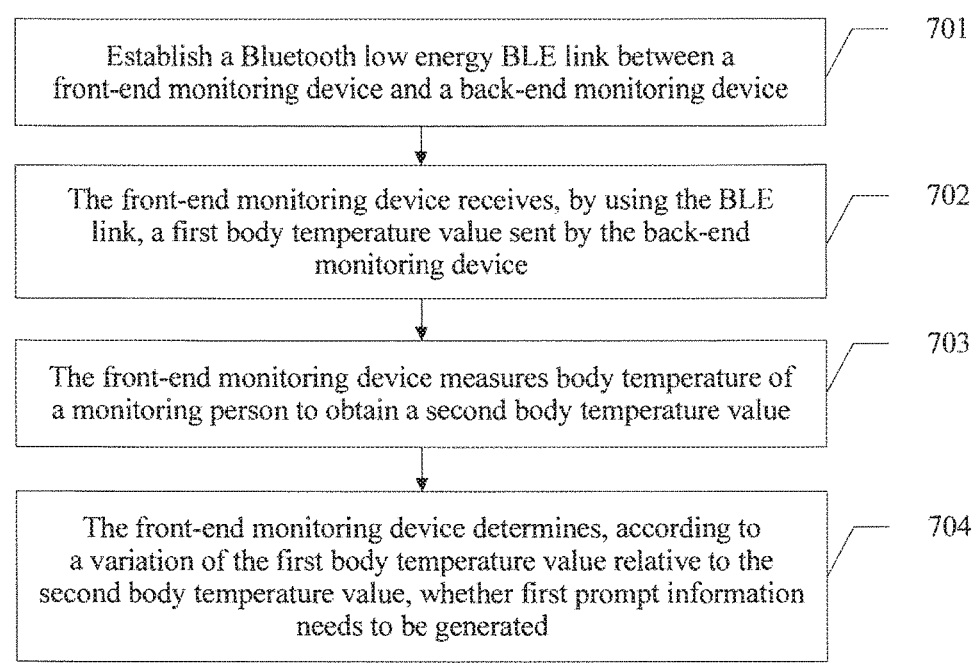
FIG. 7 is a schematic diagram of a monitoring method for an intelligent monitoring system according to an embodiment of the present disclosure.

Referring to FIG. 7, an embodiment of a monitoring method for an intelligent monitoring system in an embodiment of the present disclosure includes the following steps.

Step 701. Establish a BLE link between a front-end monitoring device and a back-end monitoring device.

Step 702. The front-end monitoring device receives, by using the BLE link, a first body temperature value sent by the back-end monitoring device.

In this step, the first body temperature value is obtained by the back-end monitoring device by measuring body temperature of a monitored person.

Step 703. The front-end monitoring device measures body temperature of a monitoring person to obtain a second body temperature value.

Step 704. The front-end monitoring device determines, according to a variation of the first body temperature value relative to the second body temperature value, whether first prompt information needs to be generated.

In some embodiments of the present disclosure, that the front-end monitoring device determines, according to a variation of the first body temperature value relative to the second body temperature value, whether first prompt information needs to be generated includes calculating, by the front-end monitoring device, a temperature difference between the first body temperature value and the second body temperature value, and generating a temperature difference sequence according to multiple calculated temperature differences; determining, by the front-end monitoring device, whether M consecutive temperature differences in the temperature difference sequence progressively increase, where M is a positive integer greater than or equal to 2; and if yes, generating, by the front-end monitoring device, the first prompt information.

In some embodiments of the present disclosure, before calculating, by the front-end monitoring device, a temperature difference between the first body temperature value and the second body temperature value, and generating a temperature difference sequence according to multiple calculated temperature differences, the method includes determining, by the front-end monitoring device, whether the second body temperature value is in a normal body temperature value range; and generating, by the front-end monitoring device, second prompt information if the second body temperature value is outside the normal body temperature value range.

In some embodiments of the present disclosure, before determining, by the front-end monitoring device, whether M consecutive temperature difference in the temperature difference sequences progressively increase, the method further includes generating, by the front-end monitoring device, a body temperature sequence according to multiple consecutively received first body temperature values; determining, by the front-end monitoring device, whether N consecutive first body temperature values in the body temperature sequence progressively decrease, where N is a positive integer greater than or equal to 2; and if the N consecutive first body temperature values in the body temperature sequence progressively decrease, performing the step of determining, by the front-end monitoring device, whether M consecutive temperature differences in the temperature difference sequence progressively increase.

In some embodiments of the present disclosure, the method further includes receiving, by the front-end monitoring device by using the BLE link, action information sent by the back-end monitoring device, where the action information is obtained by the back-end monitoring device by measuring the monitored person by using an acceleration sensor.

In some embodiments of the present disclosure, before generating, by the front-end monitoring device, the first prompt information, the method further includes determining, by the front-end monitoring device, whether the action information meets a preset condition; and generating, by the front-end monitoring device, third prompt information when the M consecutive temperature differences in the temperature difference sequence progressively increase and if the action information meets the preset condition.

In this embodiment of the present disclosure, a first body temperature value obtained by a back-end monitoring device by measuring body temperature of a monitored person and a second body temperature value obtained by a front-end monitoring device by measuring body temperature of a monitoring person are analyzed. Whether to generate first prompt information is determined according to variations, obtained by means of analysis, of the first body temperature value and the second body temperature value. Both the measured first body temperature value and the measured second body temperature value are put into calculation in a determining step. Therefore, accuracy and precision of a monitoring result are improved.

Figure 8:
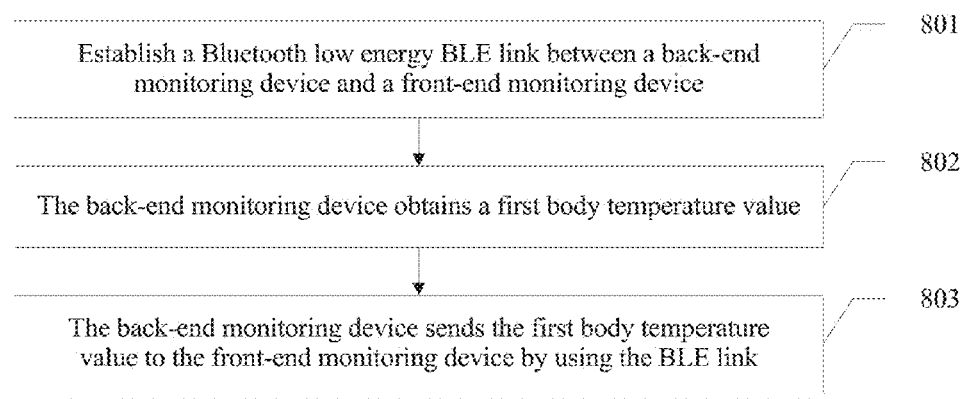
FIG. 8 is a schematic diagram of a monitoring method for an intelligent monitoring system according to another embodiment of the present disclosure.

Referring to FIG. 8, an embodiment of a monitoring method for an intelligent monitoring system in an embodiment of the present disclosure includes the following steps.

Step 801. Establish a BLE link between a back-end monitoring device and a front-end monitoring device.

Step 802. The back-end monitoring device obtains a first body temperature value.

In this step, the first body temperature value is obtained by the back-end monitoring device by measuring body temperature of a monitored person.

Step 803. The back-end monitoring device sends the first body temperature value to the front-end monitoring device by using the BLE link.

In some embodiments of the present disclosure, the method further includes obtaining, by the back-end monitoring device, action information, where the action information is obtained by the back-end monitoring device by measuring the monitored person by using an acceleration sensor; and sending, by the back-end monitoring device, the action information to the front-end monitoring device by using the BLE link.

In this embodiment of the present disclosure, a back-end monitoring device sends an obtained first body temperature value to a front-end monitoring device by using a BLE link, so that the front-end monitoring device performs processing. Energy consumption of the devices is reduced in a BLE communication manner.

For ease of understanding, the following describes a monitoring method for an intelligent monitoring system in detail by using a specific application scenario.

For ease of description, this embodiment is described by using child quilt-kicking monitoring as an example. As shown in FIG. 6, a front-end monitoring device 601, that is, a device at a parent end, is a generally universal smart band. A FTH thermistor is installed on an inner side that is of the smart band and that is in contact with skin. A back-end monitoring device 602, that is, a device at a child end, is a shell temperature detector that can be put in an elastic wristband. An FTH thermistor and a built-in acceleration sensor are installed on an inner side that is of the shell temperature detector and that is in contact with skin. The front-end monitoring device 601 and the back-end monitoring device 602 are connected by using a BLE link.

Before a child goes to sleep, the back-end monitoring device 602 is fastened on a body or a leg of the child, the front-end monitoring device 601 is worn on a wrist of a parent, and a BLE link is established between the devices.

Generally, normal body temperature of a child is approximately 36.5 degrees Celsius and normal body temperature of a wrist of an adult is approximately 36 degrees Celsius. After the child kicks off a quilt, shell temperature of the child measured by the back-end monitoring device drops rapidly.

Both the back-end monitoring device and the front-end monitoring device are set for collecting obtained body temperature once a second, to obtain a first body temperature value and a second body temperature value. For example, in the first second, a body temperature value A1 of the child obtained by the back-end monitoring device is 36.0, and A1 is sent to the front-end monitoring device by using the BLE link. In the first second, a body temperature value B1 of the parent obtained by the front-end monitoring device is 36.1. The front-end monitoring device learns, by means of calculation, that a temperature difference C1 between A1 and B1 is 0.1.

When the child kicks off the quilt in the second second, a body temperature value A2 of the child obtained by the back-end monitoring device is 35.9, and A2 is sent to the front-end monitoring device by using the BLE link. In the second second, a body temperature value B3 of the parent obtained by the front-end monitoring device is 36.1. The front-end monitoring device learns, by means of calculation, that a temperature difference C2 between A2 and B2 is 0.2.

In the third second, a body temperature value A3 of the child obtained by the back-end monitoring device is 35.7, and A3 is sent to the front-end monitoring device by using the BLE link. In the third second, a body temperature value B3 of the parent obtained by the front-end monitoring device is 36.2. The front-end monitoring device learns, by means of calculation, that a temperature difference C3 between A3 and B3 is 0.5.

In the fourth second, a body temperature value A4 of the child obtained by the back-end monitoring device is 35.4, and A4 is sent to the front-end monitoring device by using the BLE link. In the fourth second, a body temperature value B4 of the parent obtained by the front-end monitoring device is 36.1. The front-end monitoring device learns, by means of calculation, that a temperature difference C4 between A4 and B4 is 0.7.

In the fifth second, a body temperature value A5 of the child obtained by the back-end monitoring device is 35.1, and A5 is sent to the front-end monitoring device by using the BLE link. In the fifth second, a body temperature value B5 of the parent obtained by the front-end monitoring device is 36.0. The front-end monitoring device learns, by means of calculation, that a temperature difference C5 between A5 and B5 is 0.9.

The front-end monitoring device determines whether a body temperature value in B1, B2, B3, and B5 is beyond a normal body temperature value range, and the normal body temperature value range is set to "35.0 to 37.5". If B2 is 38.0, it indicates that the parent has a fever, and the body temperature value of the parent cannot be used for calculation. The front-end monitoring device generates second prompt information. In this example, the second prompt information is a buzzing sound that is made once every two seconds, so as to remind the parent that a body temperature value at the parent end is abnormal. In this embodiment, B1, B2, B3, B4, and B5 are all in the normal body temperature value range. The front-end monitoring device generates a temperature difference sequence by using C1, C2, C3, C4, and C5, generates a body temperature sequence by using A1, A2, A3, A4, and A5, and determines whether consecutive four first body temperature values in the body temperature sequence progressively decrease. A2 to the A5 progressively decrease. Therefore, the front-end monitoring device continues to determine whether consecutive three temperature differences in the temperature difference sequence progressively increase. Any consecutive three temperature differences from C1 to C5 progressively increase. Therefore, the front-end monitoring device generates first prompt information. In this example, the first prompt information is a buzzing sound that is made once every 0.5 second, so as to remind the parent of a drop in the body temperature of the child.

The back-end monitoring device records action information when the child performs an action, and sends the action information to the front-end monitoring device by using the BLE link. The front-end monitoring device determines whether the received action information meets a preset condition for a preset turn-over action. When the consecutive three temperature differences in the temperature difference sequence progressively increase, and if the action information meets the preset condition, the front-end monitoring device generates third prompt information. In this example, the third prompt information is vibration. Because the consecutive three temperature differences in the temperature difference sequence progressively increase, the front-end monitoring device generates the first prompt information. In this case, the first prompt information and the third prompt information may be sent together. The front-end monitoring device generates a buzzing sound and vibration once every 0.5 second, so as to remind the parent that the child kicks off the quilt. When the consecutive three temperature differences in the temperature difference sequence progressively increase, and if the action information does not reach the preset condition, the front-end monitoring device generates the first prompt information, that is, the buzzing sound that is made once every 0.5 second.

In this embodiment of the present disclosure, the first prompt information, the second prompt information, and the third prompt information may be sent in a manner such as buzzing, vibration, lighting, or voice broadcasting. The three pieces of prompt information may be sent in different manners.

The foregoing intelligent monitoring system is used for child quilt-kicking monitoring, and may be further used for child fever temperature variation monitoring. For example, when a child has a fever, a front-end monitoring device may be set for monitoring a first body temperature value and a first body temperature value range is set to "35.0 to 38.0". When the child has a low fever or a high fever, a back-end monitoring device sends a measured first body temperature value to the front-end monitoring device. When the front-end monitoring device determines that the first body temperature value is not in the specified first body temperature value range, the front-end monitoring device generates prompt information to remind the parent.

A microprocessor in the back-end monitoring device is correspondingly programmed, so that the back-end monitoring device may further have functions such as child fever temperature variation monitoring, child step counting, and child sleep quality monitoring. Details are not described herein.

It may be clearly understood by persons skilled in the art that, for the purpose of convenient and brief description, for a detailed working process of the foregoing system, apparatus, and unit, reference may be made to a corresponding process in the foregoing method embodiments, and details are not described herein.

In the several embodiments provided in this application, it should be understood that the disclosed system, apparatus, and method may be implemented in other manners. For example, the described apparatus embodiment is merely an example. For example, the unit division is merely logical function division and may be other division in actual implementation. For example, multiple units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected according to actual needs to achieve the objectives of the solutions of the embodiments.

In addition, functional units in the embodiments of the present disclosure may be integrated into one processing unit, or each of the units may exist alone physically, or two or more units are integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of the present disclosure essentially, or the part contributing to the prior art, or all or some of the technical solutions may be implemented in the form of a software product. The software product is stored in a storage medium and includes several instructions for instructing a computer device (which may be a personal computer, a server, or a network device) to perform all or some of the steps of the methods described in the embodiments of the present disclosure. The foregoing storage medium includes any medium that can store program code, such as a universal serial bus (USB) flash drive, a removable hard disk, a read-only memory (ROM), a random access memory (RAM), a magnetic disk, or an optical disc.

The foregoing embodiments are merely intended for describing the technical solutions of the present disclosure, but not for limiting the present disclosure. Although the present disclosure is described in detail with reference to the foregoing embodiments, persons of ordinary skill in the art should understand that they may still make modifications to the technical solutions described in the foregoing embodiments or make equivalent replacements to some technical features thereof, without departing from the spirit and scope of the technical solutions of the embodiments of the present disclosure.

What is claimed is:

1. A front-end monitoring device, comprising:
  a Bluetooth low energy (BLE) device configured to establish a BLE link between the front-end monitoring device and a back-end monitoring device;
  a universal asynchronous receiver/transmitter (UART) coupled to the BLE device and configured to receive, using the BLE link, a first body temperature value from the back-end monitoring device, wherein the first body temperature value is a measured body temperature of a monitored person;
  a thermistor sensor configured to measure body temperature of a monitoring person associated with the front-end monitoring device to obtain a second body temperature value; and
  a processor coupled to the thermistor sensor and configured to generate first prompt information according to a variation of the first body temperature value relative to the second body temperature value.

2. The front-end monitoring device according to claim 1, wherein the processor is further configured to:
  calculate a temperature difference between the first body temperature value and the second body temperature value;
  generate a temperature difference sequence according to multiple calculated temperature differences;
  determine whether M consecutive temperature differences in the temperature difference sequence progressively increase, wherein M is a positive integer greater than or equal to 2; and
  generate the first prompt information when the M consecutive temperature differences in the temperature difference sequence progressively increase.

3. The front-end monitoring device according to claim 2, wherein the processor is further configured to:
  determine whether the second body temperature value is in a normal body temperature value range; and
  generate second prompt information when the second body temperature value is outside the normal body temperature value range.

4. The front-end monitoring device according to claim 2, wherein the processor further configured to:
  generate a body temperature sequence according to multiple consecutively received first body temperature values; and
  determine whether N consecutive first body temperature values in the body temperature sequence progressively decrease, wherein N is a positive integer greater than or equal to 2.

5. The front-end monitoring device according to claim 2, wherein the UART is further configured to receive, using the BLE link, action information from the back-end monitoring device, and wherein the action information is information received by measuring the monitored person with an acceleration sensor.

6. The front-end monitoring device according to claim 5, wherein the processor is further configured to:
  determine whether the action information meets a preset condition; and
  generate third prompt information when the M consecutive temperature differences in the temperature difference sequence progressively increase and the action information meets the preset condition.

7. A back-end monitoring device, comprising:
  a Bluetooth low energy (BLE) device configured to establish a BLE link between the back-end monitoring device and a front-end monitoring device;
  a thermistor sensor configured to measure body temperature of a monitored person to obtain a first body temperature value;
  a universal asynchronous receiver/transmitter UART coupled to the thermistor sensor and to the BLE device, wherein the UART is configured to send the first body temperature value to the front-end monitoring device by using the BLE link, the first body temperature value being used to obtain information on a variation of the first body temperature value relative to a second body temperature value associated with the front-end monitoring device.

8. The back-end monitoring device according to claim 7, further comprising an acceleration sensor, wherein the acceleration sensor is configured to measure an action of the monitored person to obtain action information, and wherein the UART is further configured to send the action information to the front-end monitoring device by using the BLE link.

9. A monitoring method for an intelligent monitoring system, comprising:
  establishing, with a Bluetooth low energy (BLE) device, a BLE link between a front-end monitoring device and a back-end monitoring device;
  receiving, by the front-end monitoring device using the BLE link, a first body temperature value from the back-end monitoring device, wherein the first body temperature value is obtained by the back-end monitoring device by measuring a body temperature of a monitored person;
  measuring, by the front-end monitoring device, body temperature of a monitoring person to obtain a second body temperature value; and
  generating, by the front-end monitoring device, first prompt information according to a variation of the first body temperature value relative to the second body temperature value.

10. The monitoring method for the intelligent monitoring system according to claim 9, wherein determining, by the front-end monitoring device according to a variation of the first body temperature value relative to the second body temperature value, whether first prompt information needs to be generated comprises:
  calculating, by the front-end monitoring device, a temperature difference between the first body temperature value and the second body temperature value;
  generating a temperature difference sequence according to multiple calculated temperature differences;
  determining, by the front-end monitoring device, whether M consecutive temperature differences in the temperature difference sequence progressively increase, wherein M is a positive integer greater than or equal to 2; and
  generating, by the front-end monitoring device, the first prompt information when the M consecutive temperature differences in the temperature difference sequence progressively increase.

11. The monitoring method for an intelligent monitoring system according to claim 10, wherein the method further comprises:
  determining, by the front-end monitoring device, whether the second body temperature value is in a normal body temperature value range; and
  generating, by the front-end monitoring device, second prompt information, and wherein the second body temperature value is outside the normal body temperature value range.

12. The monitoring method for an intelligent monitoring system according to claim 10, wherein the method further comprises:
  generating, by the front-end monitoring device, a body temperature sequence according to multiple consecutively received first body temperature values;
  determining, by the front-end monitoring device, whether N consecutive first body temperature values in the body temperature sequence progressively decrease, wherein N is a positive integer greater than or equal to 2; and
  determining, by the front-end monitoring device, whether M consecutive temperature differences in the temperature difference sequence progressively increase, and wherein the N consecutive first body temperature values in the body temperature sequence progressively decrease.

13. The monitoring method for an intelligent monitoring system according to claim 10, wherein the method further comprises receiving, by the front-end monitoring device using the BLE link, action information from the back-end monitoring device, wherein the action information is obtained by measuring the monitored person with an acceleration sensor.

14. The monitoring method for an intelligent monitoring system according to claim 13, wherein the method further comprises:
  determining, by the front-end monitoring device, whether the action information meets a preset condition; and
  generating, by the front-end monitoring device, third prompt information when each of the M consecutive temperature differences in the temperature difference sequence progressively increase, and wherein the action information meets the preset condition.

15. The back-end monitoring device according to claim 7, wherein the information on the variation of the first body temperature value relative to the second body temperature value is used to provide prompt information according to the variation.

* * * * *